United States Patent
Weser et al.

(10) Patent No.: US 10,780,035 B2
(45) Date of Patent: Sep. 22, 2020

(54) OXIDATIVE HAIR DYEING AGENT HAVING REDUCED HAIR DAMAGE AND IMPROVED DYEING PROPERTIES

(71) Applicant: Henkel AG & Co. KGaA, Duesseldorf (DE)

(72) Inventors: Gabriele Weser, Neuss (DE); Ulrike Schumacher, Duesseldorf (DE); Claudia Kolonko, Remscheid (DE); Constanze Neuba, Grevenbroich (DE); Irmgard Bender, Duesseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 28 days.

(21) Appl. No.: 16/224,250

(22) Filed: Dec. 18, 2018

(65) Prior Publication Data

US 2019/0183761 A1  Jun. 20, 2019

(30) Foreign Application Priority Data

Dec. 19, 2017  (DE) .................. 10 2017 223 233

(51) Int. Cl.
| | | |
|---|---|---|
| *A61Q 5/10* | (2006.01) | |
| *A61K 8/41* | (2006.01) | |
| *A61K 8/04* | (2006.01) | |
| *A61K 8/06* | (2006.01) | |
| *A61K 8/60* | (2006.01) | |
| *A61K 8/86* | (2006.01) | |
| *A61K 8/81* | (2006.01) | |
| *A61K 8/22* | (2006.01) | |
| *A61K 8/34* | (2006.01) | |

(52) U.S. Cl.
CPC .............. *A61K 8/41* (2013.01); *A61K 8/042* (2013.01); *A61K 8/062* (2013.01); *A61K 8/22* (2013.01); *A61K 8/345* (2013.01); *A61K 8/602* (2013.01); *A61K 8/8152* (2013.01); *A61K 8/86* (2013.01); *A61Q 5/10* (2013.01); *A61K 2800/262* (2013.01); *A61K 2800/592* (2013.01); *A61K 2800/884* (2013.01)

(58) Field of Classification Search
CPC ........ A61Q 5/10; A61K 8/411; A61K 8/4926; A61K 8/415; A61K 8/22; A61K 8/347; A61K 8/86; A61K 8/345; A61K 8/73; A61K 8/375
See application file for complete search history.

(56) References Cited

U.S. PATENT DOCUMENTS

2014/0298592 A1* 10/2014 Schweinsberg .......... A61Q 5/10
8/405

FOREIGN PATENT DOCUMENTS

WO  2007125239 A1  11/2007

OTHER PUBLICATIONS

English Abstract of the Patent No. WO 2010/026009 A1 (Mar. 11, 2010).*
Seppic, "Aquaxyl", seppic.com, Jan. 25, 2017, Available from https://www.seppic.com/aq [Accessed: May 23, 2019 online].
Anonymous, "Effect of the composition commercialized under the trade name of Aquaxyl on the expression of barrier function-related genes and moisturisation-related proteins", IP.com, Dec. 20, 2013, pp. 1-4, IP.com Electronic Publication.

* cited by examiner

*Primary Examiner* — Eisa B Elhilo
(74) *Attorney, Agent, or Firm* — Lorenz & Kopf, LLP

(57) ABSTRACT

The subject of present disclosure is an oxidation dyeing agent for the oxidative color change of keratinous fibers, in particular human hair, comprising at least one alkalizing agent, at least one oxidation dye precursor of a developer type and at least one oxidation dye precursor of a coupler type, at least one ether compound of xylitol and, based on the weight of oxidation dyeing agent, zero to less than 0.1% by weight of peroxide compounds, wherein the oxidation dyeing agent preferably has a pH value in the range of 8 to 11, in particular in the range of 8.5 to 10.7, particularly preferably in the range of 9 to 10.3, most preferably 9.5 to 9.7, each measured at a temperature of 22° C.

20 Claims, No Drawings

OXIDATIVE HAIR DYEING AGENT HAVING REDUCED HAIR DAMAGE AND IMPROVED DYEING PROPERTIES

CROSS-REFERENCE TO RELATED APPLICATION

This application claims priority to German Patent Application No. 10 2017 223 233.1, filed Dec. 19, 2017, which is incorporated herein by reference in its entirety.

TECHNICAL FIELD

The present disclosure relates to a dyeing agent for oxidative hair dyeing, which has an optimized conditioning performance and/or improved dyeing performance, and a method for oxidative hair dyeing using an oxidative dyeing agent having optimized conditioning and/or dyeing performance.

BACKGROUND

So-called oxidation dyeing agents are used for permanent, intensive colorations with corresponding fastness properties. Oxidative dyeing agents usually consist of two components: the one component usually comprises oxidation dye precursors, so-called developer components and coupler components. The developer components form the actual dyes under the influence of oxidation agents, in particular hydrogen peroxide, which are mixed with the first components shortly before application to the hair, or by atmospheric oxygen with each other or coupling with one or more coupler components. Usually primary aromatic amines having a further, free or substituted hydroxy or amino group located in the para or ortho position, diaminopyridine derivatives, heterocyclic hydrazones, 4-aminopyrazolone derivatives and 2,4,5,6-tetraaminopyrimidine and its derivatives are used as developer components. M-phenylenediamine derivatives, naphthols, resorcinol and resorcinol derivatives, pyrazolones, m-aminophenols and substituted pyridine derivatives are generally used as coupler components. The oxidation dyeing agents are characterized by excellent, long lasting dyeing results.

Conventional oxidative dyeing agents have a stronger alkaline pH value to stabilize the dye precursors during storage and to accelerate the reaction during the oxidative use, which pH value is well above 9.0 and is adjusted with alkalizing agents, such as alkanolamines, ammonia or inorganic bases. In particular, ammonia enables good dyeing results in this case, but also reveals disadvantages for the user due to its odor and irritation potential for skin and mucous membranes. The alkalizing agent leads to a swelling of the keratinic fiber, whereby the dye precursors can penetrate well into the hair. However, the alkaline pH value also increases the damaging effect of the oxidation agent on the hair structure. The damage to the hair structure, which is particularly noticeable, affects the scaling of the cuticle, that is, the outer layer of the keratin fibers. This manifests itself in a greater roughness, poorer feel, reduced gloss and poorer fiber stability. The roughened structure of the cuticle allows small molecules, such as water, to escape more quickly. Damaged hair loses its suppleness and elasticity. But the color fastness properties are also degraded by the roughened fiber surface.

Thus, particular efforts have been directed to the development of powerful oxidative dyeing agents which contain one or more active agents which can compensate for the damaging effect of the oxidation agent so as to result in reduced hair damage. Reduction of hair damage in the present case refers to both a reduction in damage to the surface and a reduction in damage inside the keratin fiber.

A common means of reducing superficial hair damage is acidic conditioners. With its acidic pH, which is usually in the range of about pH 4 to 5, they quickly smooth the rough fiber surface. However, this measure does not affect the properties of the oxidation dyeing agent itself, because this must be set strongly alkaline in order to achieve a good dyeing result. The application of an acidic conditioner can therefore be done only in a subsequent step, which is time consuming and which the consumer would like to avoid. Dyeing agents that dye only direct-acting and therefore do without the action of an oxidation agent, are set weak to more acidic. However, such direct dyeings, so-called tints, are usually much less resistant to washing, light and/or rubbing than oxidative dyeings. As they color additively, they usually only show visible color changes on relatively light to at most medium blond hair. In the oxidation dyeing, however, the oxidation agent also destroys the fiber's own dye melanin, so that even darker hair can be dyed in many fashionable shades, which are often lighter than the original color of the fiber.

Oxidation dyeing agents which are adjusted to a weakly alkaline or even slightly acidic pH are not preferred by the consumer because of the often less satisfactory dyeing result.

Fats or silicones are often used to reduce hair damage from an alkaline oxidation dyeing agent. The formulation of such dyeing agents brings numerous problems with it, because the fat-comprising dyeing cream must be easily mixed with the highly hydrous hydrogen peroxide developer no later than during the preparation of the application mixture and applied to the hair. This usually requires the use of larger amounts of surfactants or emulsifiers, which can also contribute to hair damage. The water-insoluble fats, oils, waxes or silicones can hinder the swelling of the hair, which is explicitly desired during the exposure time of the dyeing agent, and thus the penetration of the dye precursors into the keratin fibers. Also, the dyeing agents wash out all the worse after the exposure time, the more water-insoluble constituents, such as fats and oils, are included. In addition, low-fat and non-fat oxidation dyeing agents can be easily formulated transparently, in a dosage form that is currently preferred by a large consumer group.

BRIEF SUMMARY

An oxidation dyeing agent for the oxidative color change of keratinic fibers is provided herein. The oxidation dyeing agent includes at least one alkalizing agent. The oxidation dyeing agent further includes at least one oxidation dye precursor of the developer type. The oxidation dyeing agent further includes at least one oxidation dye precursor of the coupler type. The oxidation dyeing agent further includes at least one ether compound of xylitol. The oxidation dyeing agent further includes, based on the weight of the oxidation dyeing agent, from zero to less than 0.1% by weight of peroxide compounds.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The present application was therefore based on the object of providing an oxidation dyeing agent with low fatty substance content, which causes reduced hair damage.

The present application was further based on the object of providing an oxidation dyeing agent having low fatty matter content, which leaves the hair with the smoothest possible surface after the dyeing process.

Another object was developing an oxidative dyeing agent that has improved dyeing performance. The improvement of the dyeing performance can be understood as the improvement of the color intensity, the increase of the color difference as well as the improvement of the color lift or the improvement of the chromaticity.

It has now been found that a dyeing agent comprising at least one ether compound of xylitol leaves the hair with a significantly smoother surface after the dyeing process than the same dyeing agent comprising no ether compounds of xylitol.

It has further been found that a dyeing agent comprising at least one ether compound of xylitol can improve the dyeing performance of an oxidative dyeing treatment. Improved color intensity and/or increased color difference and/or improved color lift and/or improved chromaticity are achieved with the dyeing agents as contemplated herein than with analogous dyeing agents which do not contain an ether compound of xylitol.

State of the Art

The use of xylitol ethers in cosmetic compositions was already known. WO 2007/125239A1 discloses the use of xylitol esters with certain mono-, di- or trisaccharides, preferably with glucose, fructose, idose, gulose, galactose, mannose, ribose, xylose, sucrose, maltose, isomaltose, lactose, arabinose, lyxose, allose, altrose talose, cellobiose or maltotriose, for the manufacture of cosmetic cleaning agents, in particular for improving the foam properties of these cleaning agents.

The present disclosure is, in a first embodiment, an oxidation dyeing agent for the oxidative color change of keratinous fibers, in particular human hair, comprising at least one alkalizing agent, at least one oxidation dye precursor of a developer type and at least one oxidation dye precursor of a coupler type, at least one ether compound of xylitol and, based on the weight of oxidation dyeing agent, from zero to less than 0.1% by weight of peroxide compounds, wherein the oxidation dyeing agent preferably has a pH value in the range of about 8 to about 11, in particular in the range of about 8.5 to about 10.7, particularly preferably in the range of about 9 to about 10.3, most preferably about 9.5 to about 9.7, each measured at a temperature of 22° C.

Xylitol is a sugar alcohol having 5 carbon atoms and 5 hydroxy groups. It has the CAS no. 87-99-0.

"Ether compounds of xylitol" is understood to mean both the ether compounds between xylitol and a compound other than xylitol having at least one OH group suitable for etherification and the ether compounds between two or more xylitol molecules with each other and the intramolecular ethers of xylitol.

Preferred intramolecular ethers of xylitol are 1,4-anhydroxylitol and 1,5-anhydroxylitol, wherein 1,4-anhydroxylitol is particularly preferred.

Also particularly preferred are the xylitol ethers of polyols, in particular the xylitol ethers of a polyol selected from polyols having 2 to 20 carbon atoms and 2 to 15 hydroxy groups, which may be linear or cyclic, and whose carbon atom chain may be interrupted by one or more heteroatoms, in particular by one or more oxygen atoms.

Preferred polyols for the etherification with xylitol are selected from monosaccharides, oligosaccharides, alditols, 1,2-ethylene glycol, 1,2-propanediol, glycerol, 1,3-butanediol and polyethylene glycol having 2 to 20 ethylene glycol units.

Oligosaccharides as contemplated herein are understood to mean saccharides from 2 to 5 monosaccharides, preferably from 2 to 3 monosaccharides.

Monosaccharides which are preferred for ether formation with xylitol are selected from erythrose, threose, erythrulose, ribose, deoxyribose, arabinose, glucose, fructose, galactose, arabinose, ribose, xylose, lyxose, allose, altrose, mannose, gulose, idose, talose, fucose and rhamnose, more preferably glucose, galactose, fructose, fucose and rhamnose, most preferably glucose.

Particularly preferred disaccharides for ether formation with xylitol are selected from maltose, cellobiose, sucrose, lactose and trehalose. Exceptionally preferred are maltose, cellobiose and sucrose, in particular maltose and cellobiose.

Particularly preferred trisaccharides for ether formation with xylitol are selected from maltotriose and raffinose.

Particularly preferred alditols for ether formation with xylitol are selected from xylitol, mannitol, isomalt, lactitol, sorbitol (sorbitol or glucitol), threitol, erythritol and arabitol. Preferred oxidation dyeing agents as contemplated herein are characterized in that they contain at least one ether compound of xylitol selected from ethers of xylitol having at least one mono- or oligosaccharide and intramolecular xylitol ethers and mixtures thereof. Further preferred oxidation dyeing agents as contemplated herein are characterized in that they contain at least one ether compound of xylitol selected from xylityl monoglucoside, xylityl oligoglucoside having 2, 3, 4 or 5 consecutive glucose units, 1,4-anhydroxylitol and 1,5-anhydroxylitol and mixtures thereof. Further preferred oxidation dyeing agents as contemplated herein are characterized in that they contain at least one ether compound of xylitol selected from xylityl monoglucoside, xylityloligoglucoside having 2 or 3 consecutive glucose units and 1,4-anhydroxylitol and mixtures thereof.

Further preferred oxidation dyeing agents as contemplated herein are characterized by a total content of at least one ether compound of xylitol in total of from about 0.01 to about 3% by weight, preferably from about 0.1 to about 1.5% by weight, particularly preferably from about 0.3 to about 1% by weight, most preferably from about 0.5 to about 0.8% by weight, in each case based on the weight of the oxidation dyeing agent.

The oxidation dyeing agent as contemplated herein can be present as a water-based gel, as an emulsion, cream, lotion, paste, spray or shampoo. Preferred oxidation dyeing agents as contemplated herein are present as a water-based gel. Particularly preferred oxidation dyeing agents as contemplated herein are present as water-based gel, which, based on its weight, comprises in total zero to a maximum of 2% by weight, preferably from about 0.05 to about 1% by weight, particularly preferably from about 0.1 to about 0.5% by weight, of fatty substances.

Oxidative dyeing processes on keratin fibers usually take place in an alkaline medium. It is therefore preferred that the pH value of the oxidation dyeing agent as contemplated herein is in the range from about 8 to about 11, in particular in the range from about 8.5 to about 10.7, more preferably in the range from about 9 to about 10.3, exceptionally preferably about 9.5 to about 9.7, each measured at a temperature of 22° C.

The alkalizing agents which are suitable for adjusting the preferred pH value as contemplated herein are selected from ammonia, basic amino acids, alkali hydroxides, alkanolamines, alkali metal metasilicates, alkali phosphates and alkali hydrogen phosphates. The alkali metal ions in the aforementioned alkalizing salts are preferably lithium, sodium or potassium, in particular sodium or potassium.

The basic amino acids which can be used as alkalizing agents are preferably selected from the group of L-arginine, D-arginine, D,L-arginine, L-lysine, D-lysine, D,L-lysine and mixtures thereof.

The metal hydroxides which can be used as alkalizing alkali are preferably selected from sodium hydroxide and potassium hydroxide and mixtures thereof.

The alkanolamines which can be used as alkalizing agents preferably have 2 to 9 carbon atoms in the molecule and are particularly preferably selected from primary amines having a C2-C6 alkyl basic body which carries at least one hydroxyl group. Particularly preferred alkanolamines are selected from the group formed from 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, and 2-amino-2-methylpropane-1,3-diol and mixtures thereof. Very particularly preferred alkanolamines as contemplated herein are selected from the group of 2-aminoethane-1-ol, 2-amino-2-methylpropan-1-ol and 2-amino-2-methylpropane-1,3-diol; most preferred is 2-aminoethane-1-ol. But secondary amines, such as diisopropanolamine (1,1'-iminodipropan-2-ol) are as contemplated herein also suitable alkalizing agents.

Oxidation dyeing agents which are preferred as contemplated herein are characterized in that at least one alkalizing agent selected from ammonium hydroxide and alkanolamines is present in a total amount of 2-8% by weight, preferably 2.5-7% by weight, particularly preferably 3-6% by weight, most preferably 3.5-5% by weight, in each case based on the weight of the oxidation dyeing agent.

Since the oxidation dyeing agents of the disclosure preferably contain fatty substances in a total amount of from zero to about 2% by weight, preferably from about 0.01 to about 1.5% by weight, particularly preferably from about 0.1 to about 1.0% by weight, most preferably from 0.2 to about 0.5% by weight, in each case based on the weight of the oxidation dyeing agent, preferably no ammonia or ammonium hydroxide is included as an alkalizing agent. Low fatty substance oxidation dyeing agents having ammonia or ammonium hydroxide release larger quantities of ammonia during the dyeing process than high fatty substance oxidation dyeing agents, so that non-volatile alkalizing agents, that is, all alkalizing agents other than ammonia or ammonium hydroxide, are preferred as contemplated herein.

Particularly preferred oxidation dyeing agents as contemplated herein are characterized in that at least one alkalizing agent is included, selected from alkanolamines, most preferably 2-aminoethan-1-ol, in a total amount of from about 2 to about 8% by weight, preferably from about 2.5 to about 7% by weight, more preferably from about 3 to about 6% by weight, most preferably from about 3.5 to about 5% by weight, in each case based on the weight of the oxidation dyeing agent.

Oxidation dyeing agents preferred as contemplated herein are characterized in that, based in each case on the weight of the oxidation dyeing agent, fatty substances are included in a total amount of from zero to about 2% by weight, preferably from about 0.01 to about 1.5% by weight, particularly preferably from about 0.1 to about 1.0% by weight, most preferably from about 0.2 to about 0.5% by weight.

As contemplated herein, fatty substances are understood to mean oils, fats, waxes, fatty alcohols and fatty acids. As contemplated herein, under normal conditions, a liquid oil is understood to mean an organic liquid compound which is miscible under normal conditions with bidistilled water at less than 1% by weight. As contemplated herein, fats are understood to mean triacylglycerols, that is, triesters of glycerol having fatty acids.

A wax as contemplated herein is understood to mean an organic compound which, under normal conditions, is soluble in less than 1% by weight in bidistilled water, melts at over 40° C. and then forms a liquid having a low viscosity of from about 1 to about 800 mPas at 20° C. According to the definition of the German Society for Fat Science, a wax is still kneadable at 20° C., solid to brittle-hard, has a coarse to fine crystalline structure, is translucent to opaque in color, but not glassy,  has a strong temperature-dependent consistency and solubility and is polishable under light pressure.

Fatty alcohol is understood to mean 1-alkanols having at least 4 carbon atoms which may be linear (for example, cetyl alcohol) or branched (for example, 2-ethylhexan-1-ol). Fatty acids are understood to mean 1-carboxylic acids having at least 4 carbon atoms which may be linear (for example, oleic acid) or branched (for example, 2-ethylhexanoic acid).

All information on the aggregate states of substances (solid, liquid, gaseous) in this application refers to normal conditions. "Normal conditions" are, in the context of the present application, a temperature of 20° C. and a pressure of 1013.25 mbar.

Essential oils and perfume oils or fragrances are not counted among the fatty substances. As contemplated herein, essential oils are understood to mean mixtures of volatile components which are produced by steam distillation from vegetable raw materials, such as, for example, citrus oils. If a cosmetic oil is mentioned in the present application, this is always a cosmetic oil which is not a fragrance or an essential oil, is liquid under normal conditions and immiscible with water.

The definition of a fragrance in the sense of the present application is in accordance with the expert definition as it can be found in the RÖMPP Chemie Lexikon, as of December 2007. Thereafter, a fragrance is a chemical compound with odor and/or taste that excites the hair cell receptors of the olfactory system (adequate stimulus). The necessary physical and chemical properties for this are a low molecular weight of at most 300 g/mol, a high vapor pressure, minimal water and high lipid solubility and weak polarity and the presence of at least one osmophoric group in the molecule. In order to delineate volatile, low-molecular substances which are usually and also not regarded and used as a perfuming agent in the sense of the present application, but primarily as solvents, such as, for example, ethanol, propanol, isopropanol and acetone, of odoriferous substances as contemplated herein, fragrances as contemplated herein have a molecular weight of 74 to 300 g/mol, contain at least one osmophoric group in the molecule and have an odor and/or taste, that is, they excite the receptors of the hair cells of the olfactory system.

Further preferred oxidation dyeing agents as contemplated herein contain at least one surfactant or an emulsifier. Surfactants and emulsifiers in the sense of the present disclosure are amphiphilic (bifunctional) compounds which consist of at least one hydrophobic and at least one hydrophilic molecule part. The hydrophobic radical is preferably a hydrocarbon chain having 8-28 carbon atoms, which may be saturated or unsaturated, linear or branched. With particular preference, this C8-C28 alkyl chain is linear. Basic properties of the surfactants and emulsifiers are the oriented absorption at interfaces and the aggregation to micelles and the formation of lyotropic phases.

When selecting suitable surfactants as contemplated herein, it may be preferable to use a mixture of surfactants in order to optimally adjust the stability of the oxidation dyeing agents as contemplated herein. Preferred surfactants and emulsifiers are selected from anionic, cationic, zwitterionic, amphoteric and nonionic surfactants and emulsifiers and mixtures thereof. These substances are described in detail below. Particularly preferred oxidation dyeing agents as contemplated herein contain at least one nonionic surfactant.

Nonionic surfactants preferred as contemplated herein are selected from polydimethylsiloxanes which are modified having polyethylene glycol side chains, furthermore selected from additives of 6 to 12 ethylene oxide units and one or two propylene oxide units on divalent C10-16 alkane glycols, further selected from alkyl mono- and oligoglycosides of the formula $R^4$O-[G]p in which $R^4$ stands for an alkyl or alkenyl radical having 4 to 22 carbon atoms, G stands for a sugar radical having 5 or 6 carbon atoms and p stands for a number from 1 to 6, further selected from ethoxylated castor oil with 20 to 100 moles of ethylene oxide per mole, ethoxylated C8-C24 alkanols with 10-100 moles of ethylene oxide per mole, with 20-100 moles of ethylene oxide per mole of ethoxylated sorbitan monoesters of linear saturated and unsaturated C12-C30 carboxylic acids, which may be hydroxylated, in particular those of myristic acid, palmitic acid, stearic acid or mixtures of these fatty acids, and mixtures of the aforementioned substances.

Particularly preferably used nonionic surfactants are selected from polydimethylsiloxanes which are modified with polyethylene glycol side chains, wherein the polyethylene glycol side chains have a degree of polymerization of 3 to 20, preferably from 5 to 15 and particularly preferably 12. Highly preferred is a polydimethylsiloxane modified with polyethylene glycol side chains having a degree of polymerization of 12 and having a kinematic viscosity of 260 cSt at 25° C. Such a silicone surfactant is available from Dow Corning under the trade name Xiameter OFX 0193 Fluid (formerly: Dow Corning 193 C Fluid) sold with the INCI name PEG-12 Dimethicone.

Further particularly preferably used nonionic surfactants are selected from additives of 6 to 12 ethylene oxide units and one to two propylene oxide units to divalent C10-16 alkane glycols, wherein preferred divalent C10-16 alkane glycols are selected from 1,2-decanediol, 1,2-undecanediol, 1,2-dodecanediol (lauryl glycol), 1,2-tridecanediol, 1,2-tetradecanediol, 1,2-pentadecanediol and 1,2-hexadecanediol and mixtures thereof. Particularly preferred nonionic surfactants are selected from additives of 6 to 12, preferably 8 to 9 ethylene oxide units and one to two propylene oxide units of 1,2-decanediol, 1,2-undecanediol, 1,2-dodecanediol (lauryl glycol), 1,2-tridecanediol, 1,2-tetradecanediol, 1,2-pentadecanediol or 1,2-hexadecanediol and mixtures thereof. An extraordinarily preferred nonionic surfactant of this class as contemplated herein is PPG-1-PEG-9 lauryl glycol ether, which is available, for example, under the trade name Eumulgin L from BASF.

The alkylmono- and -oligoglycosides of the formula $R^4$O-[G]p in which $R^4$ stands for an alkyl or alkenyl radical having 4 to 22 carbon atoms, G stands for a sugar radical having 5 or 6 carbon atoms and p stands for a number from 1 to 6, comprising with G a sugar radical having 5 or 6 carbon atoms, which is derived from aldoses or ketoses having 5 or 6 carbon atoms, preferably from glucose. The preferred alkyl mono- and oligoglycosides are thus alkyl mono- and oligoglucosides. The index number p in the general formula indicates the degree of oligomerization (DP), that is, the distribution of mono- and oligoglycosides, and stands for a number between 1 and 6. Whereas p must always be an integer in the individual molecule and can assume the values p=1 to 6 here, the value p for an industrially produced alkyl oligoglycoside is an analytically determined arithmetic variable, which usually represents a fractional number. Preference is given to using alkyl mono- and oligoglycosides having an average degree of oligomerization p of from about 1.1 to about 3.0. From an application point of view, those alkyl mono- and oligoglycosides whose degree of oligomerization is less than 1.7 and in particular between about 1.2 and about 1.4 are preferred. The alkyl radical $R^4$ is derived from primary alcohols having 4 to 22, preferably 8 to 18, particularly preferably 8 to 12 carbon atoms. Typical examples are butanol, caproic alcohol, caprylic alcohol, capric alcohol and undecyl alcohol and technical mixtures thereof, as obtained, for example, in the hydrogenation of technical fatty acid methyl esters or in the course of the hydrogenation of aldehydes from Roelen's oxosynthesis. Preference is given to alkyl oligoglucosides of the chain length C8-C10 (DP=1 to 3) which are obtained as forerunnings in the distillative separation of technical C8-C18 coconut fatty alcohol and can be contaminated in a proportion of less than 6% by weight C12 alcohol and alkyl oligoglucosides based on technical C9/11 oxo alcohols (DP=1 to 3). These are available commercially with the INCI name Caprylyl/Capryl Glucoside. Also preferred is an alkyl oligoglucoside commercial product whose alkyl radical $R^4$ is derived from technical C8-C18 coconut fatty alcohol and which is available with the INCI name Coco-Glucoside. The alkyl radical $R^4$ can also be derived from primary alcohols having 12 to 22, preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and technical mixtures thereof which can be obtained as described above. Preference is given to alkyloligoglucosides based on lauryl alcohol having a DP of 1 to 3.

The ethoxylated C8-C24 alkanols preferably used as contemplated herein have the formula $R^1$O(CH$_2$CH$_2$O)$_n$H where $R^1$ is a linear or branched alkyl and/or alkenyl radical having 8-24 carbon atoms and n, the average number of ethylene oxide units per molecule, for numbers from 10 to 100, preferably 10 to 30, more preferably 15 to 25 moles of ethylene oxide to 1 mole of caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and brassidyl alcohol, and technical mixtures thereof. Adducts of 10 to 100 moles of ethylene oxide onto technical fatty alcohols having 12 to 18 carbon atoms, such as, for example, coconut, palm, palm kernel or tallow fatty alcohol, are also suitable. Particularly preferred are laureth-10, laureth-12, laureth-15, laureth-20, laureth-30, myreth-10, myreth-12, myreth-15, myreth-20, myreth-30, ceteth-10, ceteth-12, ceteth-15, ceteth-20, ceteth-30, steareth-10, steareth-12 steareth-15, steareth-20, steareth-30, oleth-10, oleth-12, oleth-15, oleth-20, oleth-30, ceteareth-10, ceteareth-15, ceteareth-12, ceteareth-15, ceteareth-20, ceteareth-30 and coceth-10, coceth-12, coceth-15, coceth-20 and coceth-30.

Preferably used as contemplated herein with 20-100 moles of ethylene oxide per mole of ethoxylated sorbitan monoesters of linear saturated and unsaturated C12-C30 carboxylic acids which may be hydroxylated are selected from polysorbate-20, polysorbate-40, polysorbate-60 and polysorbate-80.

Preferred oxidation dyeing agents as contemplated herein contain the above-described silicone surfactant with the INCI name PEG-12 Dimethicone and PPG-1-PEG-9 Lauryl Glycol Ether. Further preferred oxidation dyeing agents as contemplated herein contain the above-described silicone surfactant with the INCI name PEG-12 Dimethicone, additionally PPG-1-PEG-9 Lauryl Glycol Ether and at least one alkyloligoglycoside of the formula $R^4O-[G]p$ in which $R^4$ stands for an alkyl radical having 8 to 18, preferably 8 to 12 carbon atoms, G stands for a glucose radical and p stands for a number from 1.1 to 2. Further preferred oxidation dyeing agents as contemplated herein contain at least one zwitterionic and/or at least one amphoteric surfactant and/or at least one anionic surfactant.

Zwitterionic surfactants are those surface-active compounds which carry at least one quaternary ammonium group and at least one carboxylate, sulfonate or sulfate group in the molecule. Particularly suitable zwitterionic surfactants are the so-called betaines, such as N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethyl-imidazolines each having 8 to 18 carbon atoms in the alkyl or acyl group and cocosacylaminoethylhydroxyethylcarboxymethylglycinate. A preferred zwitterionic surfactant is the fatty acid amide derivative known by the INCI name Cocamidopropyl Betaine.

Amphoteric surfactants are understood to mean surface-active compounds which, apart from a C8-C24 alkyl or acyl group in the molecule, contain at least one free amino group and at least one —COOH or —SO3H group and which are capable of forming internal salts. Examples of suitable amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids each having about 8 to 24 C atoms in the alkyl group. Particularly preferred amphoteric surfactants are N-cocoalkylaminopropionate, cocoacylaminoethylaminopropionate and C12-C18 acylsarcosine.

Suitable anionic surface-active substances are all anionic surfactants suitable for use on the human body which have a water-solubilizing anionic group, for example a carboxylate, sulfate, sulfonate or phosphate group, and a lipophilic alkyl group having about 8 to 30 C atoms, preferably 8 to 24 C atoms in the molecule. In addition, glycol or polyglycol ether groups, ester, ether and amide groups and hydroxyl groups may be present in the molecule. Examples of suitable anionic surfactants are, in each case in the form of the sodium, potassium and ammonium as well as the mono-, di- and trialkanolammonium salts having 2 to 4 C atoms in the alkanol group, linear and branched fatty acids having 8 to 30 C atoms (soaps), polyethoxylated ethercarboxylic acids, acylsarcosides, acyltaurides, acylisethionates, sulfosuccinic acid mono- and dialkylesters and sulfosuccinic acid monoalkylpolyoxyethyl esters having 1 to 6 ethylene oxide groups, linear alkanesulfonates, linear alpha-olefinsulfonates, sulfonates of unsaturated fatty acids having up to 6 double bonds, alpha-sulfofatty acid methyl ester of fatty acids, C8-C20 alkyl sulfates and C8-C20 alkyl ether sulfates having up to 15 oxyethyl groups, mixtures of surface-active hydroxysulfonates, sulfated hydroxyalkylpolyethylene and/or hydroxyalkylene-propylene glycol ethers, esters of tartaric acid or citric acid with ethoxylated or propoxylated fatty alcohols, optionally polyethoxylated alkyl and/or alkenyl ether phosphates, sulfated fatty acid alkylene glycol esters, and monoglyceride sulfates and monoglyceride ether sulfates. Preferred anionic surfactants are soaps, C8-C20 alkyl sulfates, C8-C20 alkyl ether sulfates and C8-C20 ethercarboxylic acids having 8 to 20 carbon atoms in the alkyl group and up to 12 ethylene oxide groups in the molecule. Particularly preferred is sodium cetearyl sulfate.

Preferably, the total amount of surfactant or surfactants in the oxidation dyeing agents as contemplated herein is from about 0.1 to about 5% by weight, preferably from about 0.5 to about 4% by weight and particularly preferably from about 1 to about 3.3% by weight, in each case based on the weight of the oxidation dyeing agent. Further particularly preferred oxidation dyeing agents are characterized in that they contain at least one nonionic surfactant in a total amount of from about 0.1 to about 5% by weight, preferably from 0.5 to about 4% by weight and particularly preferably from about 1 to about 3.3% by weight, in each case based on the weight of the oxidation dyeing agent.

Further preferred oxidation dyeing agents as contemplated herein are characterized in that they contain at least one thickening polymer in a total amount of from about 0.2 to about 3% by weight, preferably from about 0.5 to about 2% by weight, particularly preferably from about 0.8 to about 1.5% by weight, in each case based on the weight of the oxidation dyeing agent as contemplated herein.

Preferred thickening polymers as contemplated herein are selected from xanthan and acrylic acid polymers and mixtures thereof. It has surprisingly been found that dyeings having good fastness properties can be achieved with xanthan and acrylic acid polymers. Oxidation dyeing agents particularly preferred as contemplated herein are therefore characterized in that, in each case based on the weight of the oxidation dyeing agent as contemplated herein, they contain from about 0.05 to about 1.5% by weight, preferably from about 0.1 to about 1.5% by weight, particularly preferably from about 0.5 to about 1% by weight, of xanthan.

Acrylic acid polymers suitable as contemplated herein are selected from homopolymers of acrylic acid and their salts, which are crosslinked or uncrosslinked, and from copolymers of acrylic acid (salt), which may be crosslinked or uncrosslinked.

Crosslinking takes place with the aid of multiple olefinically unsaturated compounds, for example divinylbenzene, tetraallyloxyethane, methylenebisacrylamide, diallyl ether, polyallyl polyglyceryl ethers or allyl ethers of sugars or sugar derivatives such as trimethylolpropane, erythritol, pentaerythritol, arabitol, mannitol, sorbitol, sucrose or glucose. Preferred crosslinking agents are selected from pentaerythritylallyl ether, sucrose allyl ether, trimethylolpropane allyl ether and propylene allyl ether.

Suitable comonomers for the acrylic acid copolymers are selected from C1-4 alkyl acrylates, non-ethoxylated acrylic acid esters with linear C10-C30 monoalcohols, the half ester of itaconic acid with steareth-20, the ester of methacrylic acid with steareth-20, methacrylic acid C1-4 alkyl esters, acrylamide and methacrylamide.

Particularly preferred acrylic acid polymers as contemplated herein are selected from crosslinked homopolymers of acrylic acid and its salts, uncrosslinked homopolymers of acrylic acid and its salts, crosslinked copolymers of acrylic acid and non-ethoxylated esters of acrylic acid with linear C10-C30 monoalcohols and mixtures of these acrylic acid polymers.

Oxidation dyeing agents particularly preferred as contemplated herein are therefore characterized in that, in each case based on their weight, they contain at least one acrylic acid polymer in a total amount of from about 0.2 to about 1.5% by weight, preferably from about 0.4 to about 1% by weight, particularly preferably from about 0.5 to about 0.7% by weight.

Particularly preferred oxidation dyeing agents as contemplated herein are characterized in that, in each case based on their weight, they contain in a total amount of from about 0.2 to about 3% by weight, preferably from about 0.5 to about 2% by weight, particularly preferably from about 0.8 to about 1.5% by weight, xanthan and at least one further thickening polymer selected from at least one acrylic acid polymer. Further particularly preferred oxidation dyeing agents as contemplated herein are characterized in that they contain, in each case based on their weight, in a total amount of from about 0.2 to about 3% by weight, preferably from about 0.5 to about 2% by weight, particularly preferably from about 0.8 to about 1.5% by weight, xanthan and at least one further thickening polymer selected from crosslinked homopolymers of acrylic acid and its salts, uncrosslinked homopolymers of acrylic acid and its salts, crosslinked copolymers of acrylic acid and non-ethoxylated esters of acrylic acid with linear C10-C30 monoalcohols and mixtures of these acrylic acid polymers.

Furthermore, it is preferred that oxidation dyeing agents as contemplated herein and used as contemplated herein contain at least one cationic polymer. The cationic polymers can be homopolymers or copolymers or polymers based on natural polymers, wherein the quaternary nitrogen groups are contained either in the polymer chain or, preferably, as a substituent on one or more of the monomers. The monomers comprising ammonium groups may be copolymerized with non-cationic monomers. Suitable cationic monomers are unsaturated, free-radically polymerizable compounds bearing at least one cationic group, in particular ammonium substituted vinyl monomers such as trialkylmethacryloxyalkylammonium, trialkylacryloxyalkylammonium, dialkyldiallylammonium and quaternary vinylammonium monomers having cyclic cationic nitrogen comprising groups such as pyridinium, imidazolium or quaternary pyrrolidones, for example, alkylvinylimidazolium, alkylvinylpyridinium, or alkylvinylpyrrolidone salts. The alkyl groups of these monomers are preferably lower alkyl groups such as C1 to C7 alkyl groups, more preferably C1 to C3 alkyl groups.

The monomers comprising ammonium groups may be copolymerized with non-cationic monomers. Suitable comonomers are, for example, acrylamide, methacrylamide; alkyl and dialkylacrylamide, alkyl and dialkylmethacrylamide, alkyl acrylate, alkyl methacrylate, vinylcaprolactone, vinylcaprolactam, vinylpyrrolidone, vinyl esters, for example, vinyl acetate, vinyl alcohol, propylene glycol or ethylene glycol, wherein the alkyl groups of these monomers preferably are C1 to C7 alkyl groups, particularly preferably C1 to C3 alkyl groups.

A large number of these polymers have proven to be particularly effective components of the active agent combination as contemplated herein:

polymeric dimethyldiallylammonium salts and their copolymers with esters and amides of acrylic acid and methacrylic acid. Particularly preferred polymers of this type are dimethyldiallylammonium chloride-acrylamide copolymers, in particular those with the INCI name Polyquaternium-7. Polyquaternium-7 is, for example, available as a commercial product Merquat®550. Another preferred polymer of this type is the homopolymer poly (dimethyldiallylammonium chloride), in particular the homopolymers with the INCI name Polyquaternium-6. Polyquaternium-6 is for example as a commercial product Merquat® 100 available. Further preferred polymers of this type are terpolymers of dimethyldiallylammonium chloride, acrylamide and ammonium acrylate, in particular those with the INCI name Polyquaternium-39. Polyquaternium-39 is, for example, available as a commercial product Merquat®3330 and Merquat®3331. Further preferred polymers of this type are copolymers of dimethyldiallylammonium chloride and acrylic acid, in particular those with the INCI name Polyquaternium-22. Polyquaternium-22 is, for example, available as a commercial product Merquat®280.

Homopolymers of the general formula —{CH$_2$—[CR$^1$COO—(CH$_2$)$_m$N$^+$R$^2$R$^3$R$^4$]}$_n$ X$^-$, in which R$^1$=—H or —CH$_3$, R$^2$, R$^3$ and R$^4$ are independently selected from C1-4 alkyl, C1-4 alkenyl or C1-4 hydroxyalkyl groups, m=1, 2, 3 or 4, n is a natural number and X$^-$ is a physiologic ally compatible organic or inorganic anion. In the context of these polymers, preference is given to those as contemplated herein for which at least one of the following conditions applies: R$^1$ stands for a methyl group, R$^2$, R$^3$ and R$^4$ stand for methyl groups, m has the value 2. Suitable physiologically compatible counterions X— include, for example, halide ions, sulfate ions, phosphate ions, methosulfate ions and organic ions such as lactate, citrate, tartrate and acetate ions. Preference is given to methosulfates and halide ions, in particular chloride.

Further preferably suitable cationic polymers derived from synthetic polymers are present, for example, copolymers of A1) from about 0.1 to about 50%, preferably from about 10 to about 50% (based on the total number of monomers in the copolymer) of monomers of the formula (Ia)

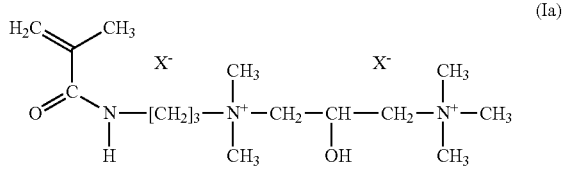

in which X stands for chloride, sulfate, methosulfate, and

A2) monomers from the group of acrylic acid, methacrylic acid and the alkali metal and ammonium salts of these acids, wherein the monomer A2 represents from about 50 to about 99.9%, preferably from about 50 to about 90% (based on the total number of monomers in the copolymer) of the copolymer. A most preferred polymer, constructed as previously illustrated, is commercially available under the INCI name Polyquaternium-74.

A particularly suitable homopolymer is, if desired, cross-linked, poly (methacryloyloxyethyltrimethylammonium chloride) with the INCI name Polyquaternium-37. Such products are commercially available, for example under the names Rheocare® CTH (Cosmetic Rheologies) and Synthalen® CR (3V Sigma). The homopolymer is preferably used in the form of a nonaqueous polymer dispersion. Such polymer dispersions are commercially available under the names Salcare® SC 95 and Salcare® SC 96.

Suitable cationic polymers derived from natural polymers are cationic derivatives of polysaccharides, for example, cationic derivatives of cellulose, starch or guar. Also suitable are chitosan and chitosan derivatives. Cationic polysaccharides have the general formula G-O—B-N+RaRbRc A-; G is an anhydroglucose radical, for example starch or cellulose anhydroglucose; B is a divalent linking group, for example, alkylene, oxyalkylene, polyoxyalkylene or hydroxyalkylene; Ra, Rb and Rc are independently alkyl, aryl, alkylaryl, arylalkyl, alkoxyalkyl or alkoxyaryl each having up to 18 C atoms, wherein the total number of carbon atoms in Ra, Rb and Rc is preferably not more than 20; A- is a common counteranion, preferably chloride.

Cationic, that is, quaternized, celluloses are available on the market with varying degrees of substitution, cationic charge density, nitrogen content and molecular weights. For example, Polyquaternium-67 is commercially available under the names Polymer® SL or Polymer® SK (Amerchol). Another highly preferred cellulose is offered under the trade name Mirustyle® CP from Croda. This is a cellulose derivatized as trimonium and cocodimonium hydroxyethylcellulose with the INCI name Polyquaternium-72. Polyquaternium-72 can be used pre-dissolved both in solid form and already in aqueous solution.

Other cationic celluloses are under the names Polymer JR® 400 (Amerchol, INCI name Polyquatemium-10) and Polymer Quatrisoft® LM-200 (Amerchol, INCI name Polyquaternium-24). Other commercial products are the compounds Celquat® H 100 and Celquat® L 200. Particularly preferred cationic celluloses are Polyquaternium-10, Polyquaternium-24, Polyquaternium-67 and Polyquaternium-72.

Suitable cationic guar derivatives are preferably selected from compounds with the INCI name Guar Hydroxypropyltrimonium Chloride.

A suitable chitosan is sold, for example, by Kyowa Oil & Fat, Japan under the trade name Flonac®. A preferred chitosan is chitosonium pyrrolidone carboxylate, which is, for example, sold under the name Kytamer® PC by Amerchol, USA. Further chitosan derivatives are commercially available under the trade names Hydagen® CMF, Hydagen® HCMF and Chitolam® NB/101.

Finally, cationic polymers based on sugars can also be used as contemplated herein with preference. Such compounds are, for example, cationic alkyl oligoglucosides as shown in the following figure.

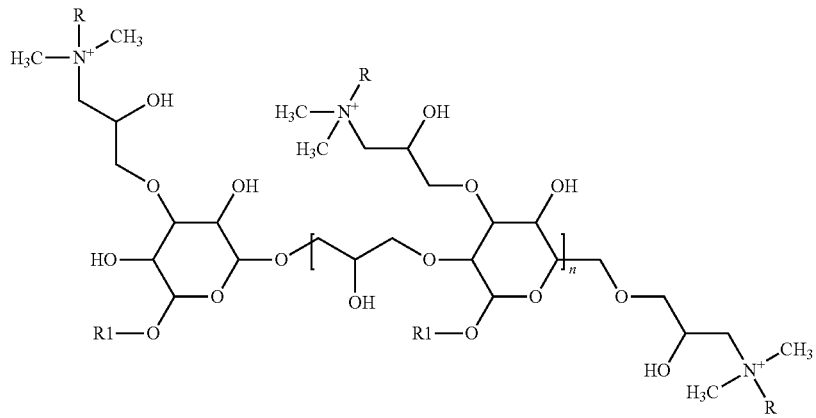

In the formula shown above, the radicals R stand for, independently of one another, a linear or branched C6 to C30 alkyl radical, a linear or branched C6-C30 alkenyl radical, the radical R for a radical R selected from: lauryl, myristyl, cetyl, stearyl, oleyl, behenyl or arachidyl.

The radicals R1 independently of one another stand for a linear or branched C6 to C30 alkyl radical, a linear or branched C6 to C30 alkenyl radical, preferably the radical R stands for a radical selected from butyl, capryl, caprylyl, octyl, nonyl, decanyl, lauryl, myristyl, cetyl, stearyl, oleyl, behenyl or arachidyl. The radicals R1 are particularly preferably the same. More preferably, the radicals R1 are selected from technical mixtures of the fatty alcohol cuts of C6/C8 fatty alcohols, C8/C10 fatty alcohols, C10/C12 fatty alcohols, C12/C14 fatty alcohols, C12/C18 fatty alcohols, and those which are most preferred are those technical fatty alcohol cuts of plant origin.

Particularly preferred examples of the cationic alkyl oligoglucosides are the compounds with the INCI names Polyquaternium-77, Polyquaternium-78, Polyquaternium-79, Polyquaternium-80, Polyquaternium-81 and Polyquaternium-82. Most preferred are the cationic alkyl oligoglucosides named Polyquaternium-77, Polyquaternium-81 and Polyquaternium-82. Such compounds can be obtained, for example, under the name Poly Suga® Quat from the company Colonial Chemical Inc.

The cationic alkyl oligoglucosides are preferably present in a total amount of from about 0.01 to about 6% by weight, particularly preferably from about 0.05 to about 4% by weight, most preferably from about 0.1 to about 3.5% by weight, in each case based on the weight of the agent as contemplated herein. Of course, it is also included as contemplated herein that mixtures of cationic alkyl oligoglucosides can be used. Preference is given in this case, if in each case a long-chain and a short-chain cationic alkyloligoglucoside are included simultaneously.

Another cationic polymer can be obtained on the basis of ethanolamine. The polymer is commercially available under the name Polyquaternium-71.

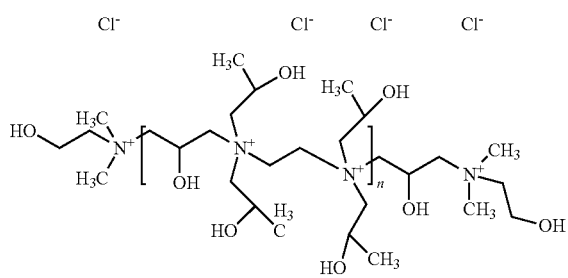

This polymer can be obtained, for example, under the name Cola® Moist 300 P from Colonial Chemical Inc.

Polyquaternium-71 is preferably present in an amount of from about 0.01 to about 6% by weight, particularly preferably from about 0.05 to about 4% by weight, most preferably from about 0.1 to about 3.5% by weight, in each case based on the weight of the agent as contemplated herein.

Further preferred cationic polymers are, for example
cationized honey, for example the commercial product Honeyquat® 50,
vinylpyrrolidone-vinylimidazoliummethochloride copolymers, as are available, for example, under the names Luviquat® FC 370, FC 550 and the INCI name Polyquaternium-16 and FC 905 and HM 552,
quaternized vinylpyrrolidone/dimethylaminoethylmethacrylate, for example vinylpyrrolidone/dimethylaminoethylmethacrylate methosulfate copolymer sold under the trade names Gafquat® 755 N and Gafquat® 734, from Gaf Co., USA and has the INCI name Polyquaternium-11,
quaternized polyvinyl alcohol,
and the polymers known under the names Polyquaternium-2, Polyquaternium-17, Polyquaternium-18 and Polyquaternium-27 having quaternary nitrogen atoms in the polymer main chain,
vinylpyrrolidone-vinylcaprolactam-acrylate terpolymers, as are commercially available with acrylic acid esters and acrylamides as the third monomer component, for example, under the name Aquaflex® SF 40.

In a particularly preferred embodiment of the disclosure, the agent as contemplated herein or used as contemplated herein, in each case based on its weight, comprises at least one cationic polymer in a total amount of from about 0.01 to about 2% by weight, preferably from about 0.05 to about 1% by weight, more preferably from about 0.1 to about 0.7% by weight, most preferably from about 0.2 to about 0.5% by weight.

In another particularly preferred embodiment of the disclosure, the agent as contemplated herein or used as contemplated herein comprises, in each case based on its weight, at least one cationic polymer selected from dimethyldiallylammonium chloride-acrylamide copolymers, in particular those with the INCI name Polyquaternium-7, poly (dimethyldiallylammonium chloride), terpolymers of dimethyldiallylammonium chloride, acrylamide and ammonium acrylate, in particular those with the INCI name Polyquaternium-39, and copolymers of dimethyldiallylammonium chloride and acrylic acid, in particular those with the INCI name Polyquaternium-22, and mixtures thereof, in a total amount of from about 0.01 to about 2% by weight, preferably from about 0.05 to about 1% by weight, particularly preferably from about 0.1 to about 0.7% by weight, most preferably from about 0.2 to about 0.5% by weight.

As mandatory ingredients, the oxidation dyeing agent as contemplated herein comprises at least one oxidation dye precursor of a developer type and at least one oxidation dye precursor of a coupler type.

Due to their reaction behavior, oxidation dye precursors can be classified into two categories, so-called developer components and coupler components.

Coupler components do not form significant dyeing in the course of oxidative dyeing alone, but always require the presence of developer components. Developer components can form the actual dye with themselves.

The developer and coupler components are usually used in free form. In the case of substances having amino groups, however, it may be preferable to use them in salt form, in particular in the form of the hydrochlorides or hydrobromides or the sulfates.

Particularly preferred developer components are selected from at least one compound from the group formed from p-phenylenediamine, p-toluenediamine, 2-(2-hydroxyethyl)-p-phenylenediamine, 2-(1,2-dihydroxyethyl)-p-phenylenediamine, N,N-bis (2-hydroxyethyl)-p-phenylenediamine, 2-methoxymethyl-p-phenylenediamine, N-(4-amino-3-methylphenyl)-N-[3-(1H-imidazol-1-yl) propyl] amine, N,N'-bis (2-hydroxyethyl)-N,N'-bis (4-aminophenyl)-1,3-diamino-propan-2-ol, bis-(2-hydroxy-5-aminophenyl) methane, 1,3-bis (2,5-diaminophenoxy) propan-2-ol, N,N'-bis (4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl) phenol and 4-amino-2-(diethylaminomethyl) phenol, 4,5-diamino-1-(2-hydroxyethyl) pyrazole, 2,4,5,6-tetraaminopyrimidine, 4-hydroxy-2,5,6-triaminopyrimidine, 2-hydroxy-4,5,6-triaminopyrimidine, the physiologically compatible salts of these compounds and mixtures of these developer components and developer component salts.

Very particularly preferred developer components are selected from 4,5-diamino-1-(2-hydroxyethyl) pyrazole, p-toluenediamine, 2-(2-hydroxyethyl)-p-phenylenediamine, 2-methoxymethyl-p-phenylenediamine, N-(4-amino-3-methylphenyl)-N-[3-(1H-imidazol-1-yl) propyl] amine and mixtures of these compounds and their physiologically compatible salts. Extraordinary preference is given to 4,5-diamino-1-(2-hydroxyethyl) pyrazole and its physiologically compatible salts.

Preferably, at least one developer component is present in a total amount of from about 0.01 to about 5% by weight, preferably from about 0.1 to about 4% by weight, particularly preferably from about 0.2 to about 2.5% by weight, in each case based on the weight of the oxidation dyeing agent as contemplated herein.

Preferably, at least one coupler component is present in a total amount of from about 0.001 to about 4% by weight, preferably from about 0.01 to about 2% by weight, particularly preferably from about 0.05 to about 1% by weight, most preferably from about 0.1 to about 0.5% by weight, in each case based on the weight of the oxidation dyeing agent as contemplated herein.

For the purposes of this application, the term "ready-to-use dyeing agent" is understood to mean the mixture of all oxidation dye precursors and all oxidation agents, optionally in combination with a suitable cosmetic carrier, for example, an aqueous gel thickened with a thickening agent or a cream base, and optionally in combination with at least a direct dye.

Coupler components as contemplated herein allow at least one substitution of a chemical radical of the coupler by the oxidized form of the developer component. This forms a covalent bond between the coupler and the developer component. Couplers are preferably cyclic compounds which carry on the ring at least two groups selected from (i) optionally substituted amino groups and/or (ii) hydroxyl groups. When the cyclic compound is a six-membered ring (preferably aromatic), said groups are preferably located in ortho position or meta position to each other.

Preferred agents as contemplated herein are characterized in that the at least one oxidation dye precursor of the coupler type is selected from one of the following classes:
3-aminophenol (m-aminophenol) and/or its derivatives,
3-aminoaniline (m-diaminobenzene) and/or its derivatives,
2-aminoaniline (1,2-diaminobenzene, o-diaminobenzene) and/or its derivatives,
2-aminophenol (o-aminophenol) and/or its derivatives,
naphthalene derivatives having at least one hydroxy group,
di- or trihydroxybenzene and/or its derivatives,
pyridine derivatives,
pyrimidine derivatives,
monohydroxyindole derivatives and/or monoamine indole derivatives,
monohydroxyindoline derivatives and/or monoaminoindoline derivatives,
pyrazolone derivatives such as 1-phenyl-3-methylpyrazol-5-one,
morpholine derivatives, such as, 6-hydroxybenzomorpholine or 6-aminobenzomorpholine,
quinoxaline derivatives such as 6-methyl-1,2,3,4-tetrahydroquinoxaline, Mixtures of two or more compounds from one or more of these classes are also preferred as contemplated herein in the context of this embodiment. Particularly preferred additional coupler components as contemplated herein are selected from 3-aminophenol, 5-amino-2-methylphenol, 3-amino-2-chloro-6-methylphenol, 2-hydroxy-4-aminophenoxyethanol, 5-amino-4-chloro-2 methylphenol, 5-(2-hydroxyethyl)amino-2-methylphenol, 2,4-dichloro-3-aminophenol, 2-aminophenol, 3-phenylenediamine, 2-(2,4-diaminophenoxy) ethanol, 1,3-bis (2,4-diaminophenoxy) propane, 1-methoxy-2-amino-4-(2'-hydroxyethylamino) benzene (=2-amino-4-hydroxyethylaminoanisole), 1,3-bis (2,4-diaminophenyl) propane, 2,6-bis (2'-hydroxyethylamino)-1-methylbenzene, 2-({3-[(2-hydroxyethyl)amino]-4-methoxy-5-methylphenyl} amino) ethanol, 2-({3-[(2-hydroxyethyl)amino]-2-methoxy-5-methylphenyl}amino) ethanol, 2-({3-[(2-hydroxyethyl)amino]-4,5-dimethylphenyl}amino) ethanol, 2-[3-morpholin-4-ylphenyl)amino] ethanol, 3-amino-4-(2-methoxyethoxy)-5-methylphenylamine, 1-amino-3-bis (2-hydroxyethyl) aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or the physiologically compatible salts of the aforementioned compounds.

Very particular preference is given to 3-aminophenol, resorcinol, 2-methylresorcinol, 5-amino-2-methylphenol, 2-(2,4-diaminophenoxy) ethanol, 1,3-bis (2,4-diaminophenoxy) propane, 1-methoxy-2-amino-4-(2'-hydroxyethylamino) benzene, 2-amino-3-hydroxypyridine and 1-naphthol and their physiologically compatible salts and mixtures of the said components.

The at least one coupler component is preferably present in a total amount of from about 0.01 to about 20% by weight, more preferably from about 0.2 to about 10% by weight, and most preferably from about 0.6 to about 5% by weight, in each case based on the weight of the oxidation dyeing agent as contemplated herein.

In the context of the present disclosure, the following combinations of oxidation dye precursors of the developer type and of the coupler type are particularly preferred, wherein the amine compounds and the nitrogen heterocycles may also be present in the form of their physiologically compatible salts:
p-toluenediamine/resorcinol;
p-toluenediamine/2-methylresorcinol;
p-toluenediamine/5-amino-2-methylphenol;
p-toluenediamine/3-aminophenol;
p-toluenediamine/2-(2,4-diaminophenoxy) ethanol;
p-toluenediamine/1,3-bis (2,4-diaminophenoxy) propane;
p-toluenediamine/1-methoxy-2-amino-4-(2-hydroxyethylamino) benzene;
p-toluenediamine/2-amino-3-hydroxypyridine;
p-toluenediamine/1-naphthol;
2-(2-hydroxyethyl)-p-phenylenediamine/resorcinol;
2-(2-hydroxyethyl)-p-phenylenediamine/2-methylresorcinol;
2-(2-hydroxyethyl)-p-phenylenediamine/5-amino-2-methylphenol;
2-(2-hydroxyethyl)-p-phenylenediamine/3-aminophenol;
2-(2-hydroxyethyl)-p-phenylenediamine/2-(2,4-diaminophenoxy) ethanol;
2-(2-hydroxyethyl)-p-phenylenediamine/1,3-bis (2,4-diaminophenoxy) propane;
2-(2-hydroxyethyl)-p-phenylenediamine/1-methoxy-2-amino-4-(2-hydroxyethylamino) benzene;
2-(2-hydroxyethyl)-p-phenylenediamine/2-amino-3-hydroxypyridine;
2-(2-hydroxyethyl)-p-phenylenediamine/1-naphthol;
2-methoxymethyl-p-phenylenediamine/resorcinol;
2-methoxymethyl-p-phenylenediamine/2-methylresorcinol;
2-methoxymethyl-p-phenylenediamine/5-amino-2-methylphenol;
2-methoxymethyl-p-phenylenediamine/3-aminophenol;
2-methoxymethyl-p-phenylenediamine/2-(2,4-diaminophenoxy) ethanol;
2-methoxymethyl-p-phenylenediamine/1,3-bis (2,4-diaminophenoxy) propane;
2-methoxymethyl-p-phenylenediamine/1-methoxy-2-amino-4-(2-hydroxyethylamino) benzene;
2-methoxymethyl-p-phenylenediamine/2-amino-3-hydroxypyridine;
2-methoxymethyl-p-phenylenediamine/1-naphthol;
N-(4-amino-3-methylphenyl)-N-[3-(1H-imidazol-1-yl)-propyl]amine/resorcinol;
N-(4-amino-3-methylphenyl)-N-[3-(1H-imidazol-1-yl) propyl]amine/2-methylresorcinol;
N-(4-amino-3-methylphenyl)-N-[3-(1H-imidazol-1-yl) propyl]amine/5-amino-2-methylphenol;
N-(4-amino-3-methylphenyl)-N-[3-(1H-imidazol-1-yl) propyl]amine/3-aminophenol;
N-(4-amino-3-methylphenyl)-N-[3-(1H-imidazol-1-yl) propyl]amine/2-(2,4-diaminophenoxy) ethanol;
N-(4-amino-3-methylphenyl)-N-[3-(1H-imidazol-1-yl)-propyl]amine/1,3-bis (2,4-diaminophenoxy) propane;

N-(4-amino-3-methylphenyl)-N-[3-(1H imidazol-1-yl) propyl]amine/1-methoxy-2-amino-4-(2-hydroxyethylamino) benzene;
N-(4-amino-3-methylphenyl)-N-[3-(1H-imidazol-1-yl) propyl]amine/2-amino-3-hydroxypyridine;
N-(4-amino-3-methylphenyl)-N-[3-(1H-imidazol-1-yl) propyl]amine/1-naphthol;
4,5-diamino-1-(2-hydroxyethyl) pyrazole/resorcinol;
4,5-diamino-1-(2-hydroxyethyl) pyrazole/2-methylresorcinol;
4,5-diamino-1-(2-hydroxyethyl) pyrazole/5-amino-2-methylphenol;
4,5-diamino-1-(2-hydroxyethyl) pyrazole/3-aminophenol;
4,5-diamino-1-(2-hydroxyethyl) pyrazole/2-(2,4-diaminophenoxy) ethanol;
4,5-diamino-1-(2-hydroxyethyl) pyrazole/1,3-bis (2,4-diaminophenoxy) propane;
4,5-diamino-1-(2-hydroxyethyl) pyrazole/1-methoxy-2-amino-4-(2-hydroxyethylamino) benzene;
4,5-diamino-1-(2-hydroxyethyl) pyrazole/2-amino-3-hydroxypyridine;
4,5-diamino-1-(2-hydroxyethyl) pyrazole/1-naphthol.

Particularly preferred as contemplated herein are the combinations 4,5-diamino-1-(2-hydroxyethyl) pyrazole/3-aminophenol and p-toluenediamine/3-aminophenol. Highly preferred, in particular with regard to the improvement of wash fastness, is the combination 4,5-diamino-1-(2-hydroxyethyl) pyrazole/3-aminophenol.

In order to achieve a balanced and subtle nuance formation, it is preferred as contemplated herein when further dyeing components are present in the oxidation dyeing agent as contemplated herein.

In a further embodiment, the oxidation dyeing agents as contemplated herein may additionally contain at least one direct dye. These are dyes that are absorbed directly on the hair and do not require an oxidative process to form the color. Direct dyes are usually nitrophenylenediamines, nitroaminophenols, azo dyes, anthraquinones or indophenols.

A further subject of the present disclosure is a packaging unit (kit of parts) which, packaged separately from one another, comprises the following:
a) at least one container (C1) comprising an agent for oxidative hair dyeing, comprising:
   at least one alkalizing agent,
   at least one oxidation dye precursor of the developer type and at least one oxidation dye precursor of the coupler type,
   at least one ether compound of xylitol and,
   based on the weight of the oxidation dyeing agent, from zero to less than about 0.1% by weight of peroxide compounds,
   wherein the oxidation dyeing agent preferably has a pH value in the range of from about 8 to about 11, in particular in the range of from about 8.5 to about 10.7, particularly preferably in the range of from about 9 to about 10.3, most preferably from about 9.5 to about 9.7, each measured at a temperature of 22° C.,
   and
b) at least one container (C2) comprising an oxidation agent preparation (M2) which comprises from about 40 to about 96% by weight, preferably from about 70 to about 93% by weight, particularly preferably from about 80 to about 90% by weight, of water, furthermore hydrogen peroxide in a total amount of from about 0.5 to about 23% by weight, more preferably from about 2.5 to about 21% by weight, particularly preferably from about 4 to about 20% by weight, very preferably from about 5 to about 18% by weight and very most preferably from about 6 to about 12% by weight, and has a pH value in the range of from about 2.0 to about 6.5, preferably from about 2.5 to about 5.5, particularly preferably from about 2.8 to about 4.5, in each case measured at 20° C., wherein the weight percentages in each case relate to the weight of the oxidation agent preparation (M2).

With regard to further preferred embodiments of the kit as contemplated herein, mutatis mutandis applies to the agents as contemplated herein, to the oxidation agent preparations used as contemplated herein and to the dyeing method as contemplated herein.

A further subject of the present disclosure is a method for oxidative hair dyeing which comprises the following method steps:
i) providing a cosmetic agent (M1) for the oxidative hair dyeing of keratinic fibers, comprising
   at least one alkalizing agent,
   at least one oxidation dye precursor of the developer type and at least one oxidation dye precursor of the coupler type,
   at least one ether compound of xylitol and,
   based on the weight of the oxidation dyeing agent, from zero to less than 0.1% by weight of peroxide compounds,
   wherein the oxidation dyeing agent preferably has a pH value in the range of 8 to 11, in particular in the range of 8.5 to 10.7, particularly preferably in the range of 9 to 10.3, most preferably 9.5 to 9.7, each measured at a temperature of 22° C.,
   and
ii) providing an oxidation agent preparation (M2) comprising from about 40 to about 96% by weight, preferably from about 70 to about 93% by weight, particularly preferably from about 80 to about 90% by weight, of water, furthermore hydrogen peroxide in a total amount of from about 0.5 to about 23% by weight, more preferably from about 2.5 to about 21% by weight, particularly preferably from about 4 to about 20% by weight, very preferably from about 5 to about 18% by weight and very most preferably from about 6 to about 12% by weight, and a pH value in the range from about 2.0 to about 6.5, preferably from about 2.5 to about 5.5, particularly preferably from about 2.8 to about 4.5, having, in each case measured at 20° C., wherein the % by weight in each case refers to the weight of the oxidation agent preparation (M2), wherein optionally at least one cationic surfactant is present,
iii) mixing the cosmetic agent (M1) with the oxidation agent preparation (M2), preferably in a weight ratio (M1):(M2) in the range from about 1:0.8 to about 1:2.5, preferably from about 1:1 to about 1:2, directly subsequently
iv) applying the mixture obtained in step iii) to the hair and leaving this mixture for a time of from about 1 to about 60 minutes, preferably from about 20 to about 45 minutes, at room temperature and/or at from about 30 to about 60° C., preferably at from about 32 to about 50° C., on the hair,
v) rinsing the hair with water and/or a cleansing composition, and
vi) optionally applying an after-treatment agent to the hair and optionally rinsing, then drying.

For oxidative hair dyeing methods, immediately before application to the hair, the agent (M1) as contemplated herein, which comprises one or more oxidation dye precursors and optionally one or more direct dyes, is mixed with an aqueous oxidation agent-comprising composition (M2) into the ready-to-use dyeing agent and then applied to the hair. In most cases, the agent (M1) as contemplated herein and the oxidation agent-comprising composition (M2) are coordinated with one another so that at a mixing ratio of 1 to 1, based on parts by weight, in the finished application mixture, an initial concentration of hydrogen peroxide of from about 0.5 to about 12% by weight, preferably from about 2 to about 10% by weight, particularly preferably from about 3 to about 6% by weight of hydrogen peroxide is present (calculated as 100% H2O2), in each case based on the weight of the application mixture. However, it is equally possible to match the agent (M1) as contemplated herein and the oxidation agent-comprising composition (M2) to one another in such a way that the concentrations required in the ready-to-use oxidation dyeing agent (application mixture) are given by mixing ratios other than 1:1, for example by weight-related mixing ratio of 1:2 or 1:3 or even 2:3.

Weight-related mixing ratios (M1):(M2) preferred as contemplated herein are in the range from about 1:0.8 to about 1:2.5, more preferably in the range from about 1:1 to about 1:2.

The term "room temperature" as contemplated herein refers to the temperature in the room in which a person usually uses a hair dyeing agent, so usually a bathroom or a hairdressing salon, in which a temperature in the range of from about 10 to about 29° C. prevails.

Leaving the hair dyeing application mixture in method step iv) in the inventive or inventively preferred dyeing method can also take place at least 30° C., preferably at from about 30 to about 60° C., more preferably at from about 32 to about 50° C., when the hair is heated, for example with a heat hood or with a heat radiator.

The oxidation agent composition (M2) used in inventive and inventively preferred dyeing kits and inventive and inventively preferred dyeing methods as contemplated herein comprises, in each case by weight, from about 40 to about 96% by weight, preferably from about 70 to about 93% by weight, particularly preferably from about 80 to about 90% by weight, of water.

The oxidation agent preparation (M2) used in inventive and inventively preferred dyeing kits and inventive and inventively preferred dyeing methods as contemplated herein further comprises, in each case based on its weight, from about 0.5 to about 23% by weight, more preferably from about 2.5 to about 21% by weight, particularly preferably from about 4 to about 20% by weight, very preferably from about 5 to about 18% by weight and very most preferably from about 6 to about 12% by weight, of hydrogen peroxide.

To stabilize the hydrogen peroxide, the oxidation agent preparation (M2) has a pH value in the range from about 2.0 to about 6.5, preferably from about 2.5 to about 5.5, particularly preferably from about 2.8 to about 4.5, in each case measured at 20° C.

Xanthan in the Oxidation Agent Preparation (M2)

The relatively low viscosity of the preferred agent (M1) as contemplated herein is very suitable in the range of from about 700 to about 20,000 mPas, preferably from about 1000 to about 15,000 mPas, more preferably from about 3000 to about 13,000 mPas, exceptionally preferably from about 4000 to about 8000 mPas, each measured at 20° C., for handling this agent by itself (manufacture, filling in plastic bottles (for viscosities up to 4000 mPas) or tubes (for viscosities greater than 4000 mPas), dosing to prepare the mixture with the oxidation agent preparation). Also, the oxidation agent preparation (M2) usually has a low viscosity in the range of from about 10 to about 6000 mPas, preferably from about 200 to about 5000 mPas, particularly preferably from about 1000 to about 4500 mPas, each measured at 20° C. For the application to the hair, however, the application mixture should have a significantly higher viscosity, so that it remains on the hair throughout the exposure time (in the range of from about 5 to about 60 minutes, preferably from about 30 to about 45 minutes) and does not drip down. Here, a distinction is made as to whether the application mixture is prepared by shaking both compositions (M1) and (M2) in an application bottle from which the application mixture is applied to the hair immediately after mixing with the aid of an application nozzle as a bottle attachment (bottle application), or whether the application mixture is prepared by stirring both compositions (M1) and (M2) in a bowl from which the application mixture is applied to the hair immediately after mixing with a brush (brush application). The bottle application is particularly suitable for dyeing agents that are sold retail with a recommendation for use by the consumer himself. The brush application is particularly suitable for dyeing agents that are made in the hairdressing salon by the hairdresser and applied to the hair of the consumer.

Surprisingly, it has been found that an application mixture having a viscosity suitable for application and remaining on the hair without dripping is obtained by mixing the inventive or inventively preferred agents (M1) with an oxidation agent preparation (M2) comprising xanthan, preferably from about 1 to about 5% by weight, particularly preferably from about 1.5 to about 4% by weight, most preferably from about 2 to about 3% by weight of xanthan, in each case based on the weight of the oxidation agent preparation (M2). The consistency thus achieved of the application mixture leads to optimal application properties, for example, for brush application. The application mixtures thus achieved, in particular at weight-related mixing ratios (M1):(M2) in the range from about 1:0.8 to about 1:2.5, particularly preferably in the range from about 1:1 to about 1:2, preferably have a viscosity in the range of from about 1000 to about 15,000 mPas, preferably from about 3000 to about 12,000 mPas, more preferably from about 4000 to about 10,000 mPas, most preferably from about 5000 to about 8000 mPas, in each case measured at 20° C. (Haake viscometer).

Cationic Surfactant in the Oxidation Agent Preparation (M2)

The relatively low viscosity of the preferred agent (M1) as contemplated herein is very suitable in the range of from about 700 to about 20,000 mPas, preferably from about 1000 to about 15,000 mPas, more preferably from about 3000 to about 13,000 mPas, exceptionally preferably from about 4000 to about 8000 mPas, each measured at 20° C., for handling this agent by itself (manufacture, filling in plastic bottles (for viscosities up to 4000 mPas) or tubes (for viscosities greater than 4000 mPas), dosing to prepare the mixture with the oxidation agent preparation). Also, the oxidation agent preparation (M2) usually has a low viscosity in the range of from about 10 to about 6000 mPas, preferably from about 200 to about 5000 mPas, particularly preferably from about 1000 to about 4500 mPas, each measured at 20° C. For the application to the hair, however, the application mixture should have a significantly higher viscosity, so that it remains on the hair throughout the exposure time (in the range of from about 5 to about 60 minutes, preferably from about 30 to about 45 minutes) and does not drip down. Here, a distinction is made as to whether the application mixture is prepared by shaking both compositions (M1) and (M2) in an application bottle from which the application mixture is applied to the hair immediately after mixing with the aid of an application nozzle as a bottle attachment (bottle application), or whether the application mixture is prepared by stirring both compositions (M1) and (M2) in a bowl from which the application mixture is applied to the hair immediately after mixing with a brush (brush application). The bottle application is particularly suitable for dyeing agents that are sold retail with a recommendation for use by the consumer himself. The brush application is particularly suitable for dyeing agents that are made in the hairdressing salon by the hairdresser and applied to the hair of the consumer.

Surprisingly, it has been found that an application mixture having a viscosity which is suitable in particular for brush application is obtained by mixing the inventive or inventively preferred agent (M1) with an oxidation agent preparation (M2) which comprises at least one cationic surfactant, in particular when the agent (M1) as contemplated herein comprises an acrylic acid polymer for thickening. The pasty consistency of the application mixture achieved with the cationic surfactant and optionally the acrylic acid polymer leads to optimum application properties, in particular for brush application. The application mixtures thus achieved, in particular at weight-related mixing ratios (M1):(M2) in the range from about 1:0.8 to about 1:2.5, particularly preferably in the range from about 1:1 to about 1:2, preferably have a viscosity in the range from about 4500 to about 25,000 mPas, preferably from about 5000 to about 15,000 mPas, particularly preferably from about 7,000 to about 12,000 mPas, in each case measured at 20° C.

In a further preferred embodiment of the disclosure, the oxidation agent preparation (M2) used as contemplated herein comprises at least one cationic surfactant, preferably in a total amount of from about 0.05 to about 3% by weight, particularly preferably from about 0.1 to about 1.5% by weight, extraordinarily preferably from about 0.3 to about 0.9% by weight, in each case based on the weight of the oxidation agent preparation (M2).

Cationic surfactants are understood to be surfactants, that is, surface-active compounds, each having one or more positive charges. Cationic surfactants contain only positive charges. Usually, these surfactants are composed of a hydrophobic part and a hydrophilic head group, wherein the hydrophobic part usually includes a hydrocarbon skeleton (for example, comprising one or two linear or branched alkyl chains), and the positive charge(s) are located in the hydrophilic head group. Cationic surfactants adsorb at interfaces and aggregate in aqueous solution above the critical micelle concentration to positively charged micelles.

Cationic surfactants of the quaternary ammonium compound type, the esterquats and the alkylamidoamines are preferred as contemplated herein. Preferred quaternary ammonium compounds are ammonium halides, such as alkyltrimethylammonium chlorides, dialkyldimethylammonium chlorides, trialkylmethylammonium chlorides, and the imidazolium compounds known under the INCI names Quaternium-27 and Quaternium-83. Further preferred quaternary ammonium compounds are tetraalkylammonium salts, such as in particular known under the INCI name Quaternium-52, a poly (oxy-1,2-ethanediyl), ((octadecylnitrilio) tri-2,1-ethanediyl) tris (hydroxy) phosphate (1:1) salt having the general structural formula (III) wherein x+y+z=10

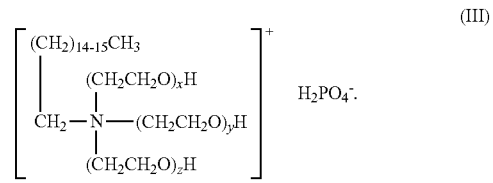

The long alkyl chains of the above said surfactants preferably have 10 to 22, more preferably 12 to 18 carbon atoms. Particularly preferred are behenyltrimethylammonium chloride, stearyltrimethylammonium chloride and cetyltrimethylammonium chloride, wherein stearyltrimethylammonium chloride is highly preferred. Further suitable cationic surfactants as contemplated herein are quaternized protein hydrolysates. Alkylamidoamines are usually prepared by amidation of natural or synthetic fatty acids and fatty acid cuts with dialkylaminoamines. Tegoamid® S 18 (stearamidopropyl) represents a suitable compound as contemplated herein from this group of substances. Esterquats are substances which contain both at least one ester function and at least one quaternary ammonium group as a structural element. Preferred esterquats are quaternized ester salts of fatty acids with triethanolamine, quaternized ester salts of fatty acids with diethanolalkylamines and quaternized ester salts of fatty acids with 1,2-dihydroxypropyldialkylamines Such products are sold under the trademarks Stepantex, Dehyquart and Armocare.

C10-C22-alkyltrimethylammonium chlorides have proven to be particularly suitable with regard to optimum application properties and optimum dyeing results. Particularly preferred oxidation agent preparations (M2) used as contemplated herein are therefore characterized in that they contain at least one cationic surfactant in a total amount of from about 0.05 to about 3% by weight, particularly preferably from about 0.1 to about 1.5% by weight, extremely preferably from about 0.3 to about 0.9% by weight, based in each case on the weight of the oxidation agent preparation (M2), wherein preference is given to at least one surfactant selected from C10-C22-alkyltrimethylammonium chlorides, in particular selected from behenyltrimethylammonium chloride, stearyltrimethylammonium chloride and cetyltrimethylammonium chloride and mixtures of these surfactants, are present. Extremely preferred oxidation agent preparations (M2) used as contemplated herein contain stearyltrimethylammonium chloride in a total amount of from about 0.05 to about 3% by weight, more preferably from about 0.1 to about 1.5% by weight, most preferably from about 0.3 to about 0.9% by weight, in each case based on the weight of the oxidation agent preparation (M2).

A further preferred packaging unit (kit of parts) as contemplated herein is characterized in that the oxidation agent preparation (M2) comprises at least one cationic surfactant, preferably in a total amount of 0.05-3% by weight, particularly preferably from about 0.1 to about 1.5% by weight, most preferably from 0.3-0.9% by weight, in each case based on the weight of the oxidation agent preparation (M2), but comprises no polymer having a degree of polymerization of at least 200 and no polymer having a molecular weight of 10,000 daltons or higher.

It has been found that thickening by means of the interaction between the acrylic acid polymer in the agent as contemplated herein and the cationic surfactant in the oxidation agent preparation (M2) is sufficient and, by the presence of a polymer having a degree of polymerization of at least 200 or a polymer having a molecular weight of 10,000 daltons or higher, may not be increased further or may even be impaired in their application properties.

A further preferred packaging unit (kit of parts) as contemplated herein is characterized in that the oxidation agent preparation (M2) comprises at least one cationic surfactant, which is preferably selected from stearyl trimethyl ammonium chloride, preferably in a total amount of about 0.05 to about 3% by weight, particularly preferably from about 0.1 to about 1.5% by weight, most preferably from about 0.3 to about 0.9% by weight, in each case based on the weight of the oxidation agent preparation (M2), but comprises no polymer having a degree of polymerization of at least 200 and no polymer having a molecular weight of 10,000 daltons or higher.

A preferred method for oxidative hair dyeing as contemplated herein is characterized in that the oxidation agent preparation (M2) comprises at least one cationic surfactant, preferably in a total amount of from about 0.05 to about 3% by weight, more preferably from about 0.1 to about 1.5% by weight, most preferably from about 0.3 to about 0.9% by weight, based in each case on the weight of the oxidation agent preparation (M2), but comprises no polymer having a degree of polymerization of at least 200 and no polymer having a molecular weight of 10,000 daltons or higher.

A further preferred method for oxidative hair dyeing as contemplated herein is characterized in that the oxidation agent preparation (M2) comprises at least one cationic surfactant, which is preferably selected from stearyl trimethyl ammonium chloride, preferably in a total amount of from about 0.05 to about 3% by weight, particularly preferably from about 0.1 to about 1.5% by weight, most preferably from about 0.3 to about 0.9% by weight, in each case based on the weight of the oxidation agent preparation (M2), but comprises no polymer having a degree of polymerization of at least 200 and no polymer having a molecular weight of 10,000 daltons or higher.

Surprisingly, it has been found that an application mixture having a viscosity suitable in particular for bottle application is obtained by mixing the inventive or inventively preferred agent (M1) with an oxidation agent preparation (M2) comprising at least one copolymer selected from crosslinked acrylic acid/acrylic acid C1-C6 alkyl ester copolymers and crosslinked methacrylic acid/acrylic acid C1-C6 alkyl ester copolymers, preferably, in a total amount of from about 0.1 to about 7% by weight, particularly preferably from about 0.5 to about 6% by weight, extremely preferably from about 1 to about 4.5% by weight, in each case based on the weight of the oxidation agent preparation (M2). The mixing of the inventive or inventively preferred agent with such an oxidation agent preparation (M2) leads to the desired increase in viscosity. The thus achieved agent-viscosity consistency of the application mixture leads to optimal application properties, in particular for bottle application. The oxidation dyeing agent as contemplated herein is mixed with an oxidation agent preparation (M2) into a ready-to-use agent which comprises at least one oxidation agent. Preferred oxidation agents are selected from peroxo compounds, preferably selected from hydrogen peroxide, solid addition compound of hydrogen peroxide to inorganic or organic compounds, such as sodium perborate, sodium percarbonate, magnesium percarbonate, sodium percarbamide, polyvinylpyrrolidone. n $H_2O_2$ (n is a positive integer greater than 0), urea peroxide and melamine peroxide, further selected from diammonium peroxodisulfate (also referred to as ammonium persulfate), disodium peroxodisulfate (also referred to as sodium persulfate) and dipotassium peroxodisulfate (also referred to as potassium persulfate) and mixtures thereof oxidation agent. Oxidation agents which are very particularly preferably used as contemplated herein are aqueous hydrogen peroxide solutions. The concentration of a hydrogen peroxide solution is determined, on the one hand, by the legal requirements and, on the other hand, by the desired effect; preferably, 6-12% by weight solutions in water are used. Oxidation dyeing agents preferred as contemplated herein are characterized in that the composition (M2) used for their preparation, based on their weight, comprises from about 1 to about 24% by weight, preferably from about 4 to about 10% by weight, more preferably from about 3 to about 6% by weight, of hydrogen peroxide (calculated as 100% $H_2O_2$).

For oxidative hair dyeing methods, usually shortly before application to the hair, the dyeing agent as contemplated herein, which comprises one or more oxidation dye precursors and optionally one or more direct dyes, is mixed with an aqueous oxidation agent-comprising composition (M2) into the ready-to-use agent and then applied to the hair. In most cases, the dyeing agent (M1) as contemplated herein and the oxidation agent-comprising composition (M2) are coordinated with one another so that at a mixing ratio of 1 to 1, based on parts by weight, in the hair dyeing agent, an initial concentration of hydrogen peroxide of from about 0.5 to about 12% by weight, preferably from about 2 to about 10% by weight, particularly preferably from about 3 to about 6% by weight of hydrogen peroxide is present (calculated as 100% $H_2O_2$) based on the weight of the oxidation dyeing agent. However, it is equally possible to coordinate the dyeing agent (M1) as contemplated herein and the oxidation agent-comprising composition (M2) to one another in such a way that the concentrations required in the ready-to-use oxidation dyeing agent are given by mixing ratios other than 1:1, for example by weight-related mixing ratio of 1:2 or 1:3 or even 2:3. Weight-related mixing ratios (M1):(M2) preferred as contemplated herein are in the range from about 1:0.8 to about 1:2.5, more preferably in the range from about 1:1 about to about 1:2.

The application mixtures of inventive or inventively preferred dyeing agent (M1) and oxidation agent-comprising composition (M2) preferably have a pH value of from about 8 to about 10.5, in particular in the range from about 8.5 to about 10.2, particularly preferably in the range of about 9.2 to about 9.8, each measured at a temperature of 22° C.

For a dyeing that requires a strong lightening of very dark hair, the use of hydrogen peroxide or its addition products to organic or inorganic compounds is often not sufficient. In these cases, a combination of hydrogen peroxide and peroxodisulfate salts (persulfate salts) is usually used. Preferred persulfate salts are ammonium peroxydisulfate, potassium peroxodisulfate, sodium peroxodisulfate, and mixtures thereof.

The at least one persulfate salt is preferably present in a total amount of from about 0.1 to about 25% by weight, particularly preferably in a total amount of from about 1 to about 5% by weight, based on the weight of the oxidation dyeing agent as contemplated herein.

With regard to further preferred embodiments of the method as contemplated herein, mutatis mutandis, the statements made with respect to the agents as contemplated herein and to the oxidation agent preparations used as contemplated herein apply.

EXAMPLES

1. The Following Dyeing Agents or Compositions (M1) were Prepared (Gels, all Amounts in % by Weight):

Dyeing gel as contemplated herein (M1-1)

| | |
|---|---|
| Acrylates/C10-30 alkyl acrylate crosspolymer | 0.70 |
| 1,2-propanediol | 2.00 |
| Xanthan gum | 0.10 |
| Sodium sulfite | 0.40 |
| 1-hydroxyethane-1,1-diphosphonic acid (etidronic acid) | 0.06 |
| Monoethanolamine | 5.00 |
| Toluene-2,5-Diaminsulfate | 1.65 |
| 4-amino-3-methylphenol (4-amino-m-cresol) | 0.21 |
| 2-methylresorcinol | 0.33 |
| Resorcinol | 0.56 |
| m-aminophenol | 0.18 |
| 2-amino-6-chloro-4-nitrophenol | 0.10 |
| Niacinamide | 0.10 |
| Panthenol | 0.10 |
| Xylitylglucoside | 0.21 |
| Anhydroxylitol | 0.15 |
| PEG-12 | 0.07 |
| PEG-12 Dimethicone | 0.80 |
| PPG-1-PEG-9 Lauryl glycol ether | 0.30 |
| Perfume | 0.15 |
| Water, demineralized | 86.83 |

Dyeing gel as contemplated herein (M1-2)

| | |
|---|---|
| 1-hydroxyethane-1,1-diphosphonic acid (etidronic acid) | 0.12 |
| Sulfuric acid | 0.50 |
| Carbomer | 0.50 |
| 1,2-propanediol | 5.20 |
| Xanthan gum | 1.00 |
| Niacinamide | 0.15 |
| Opuntia Ficus-Indica Flower Extract | 0.10 |
| Aloe Barbadensis Leaf Extract | 0.01 |
| Anhydroxylitol | 0.29 |
| Xylityl glucosides | 0.43 |
| Caprylyl/caprylic glucosides | 0.30 |
| Coco-glucosides | 0.80 |
| Polyquaternium-39 | 0.10 |
| Sodium sulfite | 0.40 |
| Potassium hydroxide | 0.25 |
| Toluene-2,5-diaminsulfate | 0.22 |
| 4-amino-3-methylphenol (4-amino-m-cresol) | 0.30 |
| 2-methylresorcinol | 0.13 |
| Resorcinol | 0.20 |
| 2-amino-3-hydroxypyridine | 0.06 |
| 2-amino-6-chloro-4-nitrophenol | 0.01 |
| Sodium silicate 40/42 | 0.20 |
| PPG-1-PEG-9 Lauryl glycol ether | 2.00 |
| Perfume | 0.90 |
| Water, demineralized | 85.83 |

The following oxidation compositions (M2) were prepared (all amounts in % by weight):

Developer Gel (M2-1) (6% by weight $H_2O_2$)

| | |
|---|---|
| Sodium hydroxide | 0.33 |
| 2,6-dicarboxypyridine | 0.10 |
| Disodiumpyrophosphate | 0.03 |
| 1-hydroxyethane-1,1-diphosphonic acid (etidronic acid) | 0.90 |
| Xanthan gum | 2.00 |
| Propane-1,2-diol | 4.00 |
| Hydrogen peroxide | 6.00 |
| Water, demineralized | 86.64 |

Developer emulsion (M2-2) (4% by weight $H_2O_2$)

| Developer 4% | |
|---|---|
| Sodium benzoate | 0.04 |
| 2,6-dicarboxypyridine | 0.10 |
| Disodiumpyrophosphate | 0.10 |
| Potassium hydroxide | 0.15 |
| 1,2-propanediol | 1.50 |
| Etidronic acid | 0.24 |
| Paraffin Liquidum | 0.30 |
| Isopropyl alcohol | 0.08 |
| Steartrimonium chlorides | 0.31 |
| Ceteareth-20 | 1.00 |
| Cetearyl alcohol | 3.40 |
| Hydrogen peroxide | 4.00 |
| Perfume | 0.10 |
| Water, demineralized | 88.68 |

2 Coloration

For the preparation of ready-to-use oxidative dyeing agents, the cosmetic agents (M1-1) or (M1-2) were each mixed in the weight ratio 1:1 with one of the oxidation agent preparation (M2-1) or (M2-2).

The oxidative dyeing agents prepared in this manner were each applied in a defined amount (4 g oxidative dyeing agent per 1 g yak hair) to yak hair strands (12 strands per oxidative dyeing agent) and remained on the hair strands for exposure period of 30 minutes at 32° C. The remaining agents were each then rinsed with lukewarm water from the hair strands for 2 minutes, the strands first dried with a towel and then blown dry.

Intensively colored strands were obtained in each case.

3. Measurement of the Profile of the Hair Fiber Surface with Confocal Microscopy

| Dyeing gels | (M1-3) as contemplated herein | (M1-4) comparative composition |
|---|---|---|
| 1-hydroxyethane-1,1-diphosphonic acid | 0.12 | 0.12 |
| Sulfuric acid | 0.50 | 0.50 |
| Carbomer | 0.50 | 0.50 |
| 1,2-propanediol | 5.20 | 5.20 |
| Xanthan gum | 1.00 | 1.00 |
| Niacinamide | 0.15 | 0.15 |
| Opuntia Ficus-Indica Flower Extract | 0.10 | 0.10 |
| Aloe Barbadensis Leaf Extract | 0.01 | 0.01 |
| Anhydroxylitol | 0.29 | — |
| Xylityl glucosides | 0.43 | — |
| Caprylyl/caprylic glucosides | 0.30 | 0.30 |
| Coco-glucosides | 0.80 | 0.80 |
| Polyquaternium-39 | 0.10 | 0.10 |
| Sodium sulfite | 0.40 | 0.40 |
| Potassium hydroxide | 0.25 | 0.25 |
| Toluene-2,5-diaminsulfate | 0.79 | 0.79 |
| 2-methylresorcinol | 0.12 | 0.12 |
| Resorcinol | 0.16 | 0.16 |
| 4-chlororesorcinol | 0.14 | 0.14 |
| m-aminophenol | 0.03 | 0.03 |
| 2-amino-6-chloro-4-nitrophenol | 0.02 | 0.02 |
| Sodium silicate 40/42 | 0.20 | 0.20 |
| PPG-1-PEG-9 Lauryl glycol ether | 2.00 | 2.00 |
| Perfume | 0.90 | 0.90 |
| Water, demineralized | 85.49 | 86.21 |
| average profile depth of the hair | 0.18 μm | 0.30 μm |

For the preparation of ready-to-use oxidative dyeing agents, the cosmetic agents (M1-3) or (M1-4) were each mixed in a weight ratio of 1:1 with the oxidation agent preparation (M2-1).

The oxidative dyeing agents prepared in this way were each applied in a defined amount (4 g of oxidative dye per 1 g yak hair) on yak hair strands. The remaining agents were then rinsed with lukewarm water from the hair strands for 2 minutes each, the strands first dried with a towel and then blown dry.

A statistically significant number of individual hair fibers was taken from the strands treated in this way. The profile of each fiber was measured by confocal microscopy. For this purpose, the profile of the fiber cross-section was recorded at 7 points along the longitudinal axis of the fiber (in μm).

From this, the profile depth between the individual scales of the hair cuticle is determined. The smaller the profile depth between the individual cuticle scales, the smoother and more undamaged the fiber is.

According to this method, an average profile depth of 0.18 μm was determined for the hair dyed with the oxidation dyeing agent (M1-3) as contemplated herein, and the hair dyed with the comparative oxidation dyeing agent (M1-4) had an average profile depth of 0.30 μm. The values were statistically significant.

Oxidation dyeing agents as contemplated herein thus cause significantly reduced hair damage.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An oxidation dyeing agent for the oxidative color change of keratinic fibers, comprising at least one alkalizing agent, at least one oxidation dye precursor of the developer type, at least one oxidation dye precursor of the coupler type, at least one ether compound of xylitol and, based on the weight of the oxidation dyeing agent, from zero to less than 0.1% by weight of peroxide compounds.

2. The oxidation dyeing agent according to claim 1, wherein the at least one ether compound of xylitol is selected from xylitol ethers of polyols, which can be linear or cyclic and whose carbon atom chain can be interrupted by one or more heteroatoms.

3. The oxidation dyeing agent according to claim 1, wherein the at least one ether compound of xylitol is selected from ethers of xylitol having at least one mono- or oligosaccharide and intramolecular xylitol ethers and mixtures thereof.

4. The oxidation dyeing agent according to claim 1, wherein the mono- or oligosaccharide etherified with xylitol is selected from glucose and glucose oligomers having from 2 to 5 glucose units.

5. The oxidation dyeing agent according to claim 1, wherein the at least one intramolecular xylitol ether is selected from 1,4-anhydroxylitol and 1.5-anhydroxylitol and mixtures thereof.

6. The oxidation dyeing agent according to claim 1, wherein a total content of at least one ether compound of xylitol is in a total amount of from about 0.01 to about 3% by weight based on the weight of the oxidation dyeing agent.

7. The oxidation dyeing agent according to claim 1, further comprising fatty substances present therein, wherein the fatty substances are present in a total amount of from zero to about 2% by weight based on the weight of the oxidation dyeing agent.

8. The oxidation dye according to claim 1, wherein at least one alkalizing agent, selected from ammonium hydroxide and alkanolamines, is present in a total amount of from about 2 to about 8% by weight based on the weight of the oxidation dyeing agent.

9. The oxidation dyeing agent according to claim 1, wherein no ammonia and no ammonium hydroxide is present.

10. The oxidation dyeing agent according to claim 1, wherein at least one surfactant is present.

11. The oxidation dyeing agent according to claim 10, wherein at least one surfactant is present in a total amount of from about 0.1 to about 5% by weight based on the weight of the oxidation dyeing agent.

12. The oxidation dyeing agent according to claim 1, wherein water is present in a total amount of from about 68 to about 93% by weight based on the weight of the oxidation dyeing agent.

13. The oxidation dyeing agent according to claim 1, wherein at least one thickening polymer is included in a total amount of from about 0.2 to about 3% by weight based on the weight of the oxidation dyeing agent.

14. A method for oxidative hair dyeing, comprising the following method steps:
  i) providing a cosmetic agent (M1) for the oxidative hair dyeing of keratinic fibers according to claim 1, the cosmetic agent (M1) comprising:
    at least one alkalizing agent,
    at least one oxidation dye precursor of the developer type and at least one oxidation dye precursor of the coupler type,
    at least one ether compound of xylitol, and,
    based on the weight of the oxidation dyeing agent, from zero to less than 0.1% by weight of peroxide compounds,
  and
  ii) providing an oxidation agent preparation (M2) comprising from about 40 to about 96% by weight of water, furthermore hydrogen peroxide in a total amount of from about 0.5 to about 23% by weight, and a pH value in the range from about 2.0 to about 6.5 measured at 20° C., wherein the % by weight in each case refers to the weight of the oxidation agent preparation (M2),
  iii) mixing the cosmetic agent (M1) with the oxidation agent preparation (M2)\, directly subsequently
  iv) applying the mixture obtained in step iii) to the hair and leaving this mixture for a time of from about 1 to about 60 minutes at room temperature or at 30-60° C., on the hair, and
  v) rinsing the hair with water and/or a cleansing composition, and
  vi) then drying.

15. A packaging unit (kit of parts) which, packaged separately from one another, comprises the following:
  a) at least one container (C1) comprising an agent for oxidative hair dyeing according to claim 1, comprising:
    at least one alkalizing agent,
    at least one oxidation dye precursor of the developer type and at least one oxidation dye precursor of the coupler type,
    at least one ether compound of xylitol and,
    based on the weight of the oxidation dyeing agent, from zero to less than 0.1% by weight of peroxide compounds, wherein the oxidation dyeing agent has a pH value in the range of from about 8 to about 11 at a temperature of 22° C., and b) at least one container (C2) comprising an oxidation agent preparation (M2) which comprises from about 40 to about 96% by weight of water, furthermore hydrogen peroxide in a total amount of from about 0.5 to about 23% by weight, and has a pH value in the range of from about 2.0 to about 6.5 measured at 20° C., wherein the weight percentages in each case relate to the weight of the oxidation agent preparation (M2).

16. The oxidation dyeing agent according to claim 1, wherein the oxidation dyeing agent has a pH value in the range of about 8 to about 11 measured at a temperature of 22° C.

17. The oxidation dyeing agent according to claim 2, wherein the xylitol ethers of a polyol are selected from polyols having 2 to 20 carbon atoms and 2 to 15 hydroxy groups.

18. The oxidation dyeing agent according to claim 2, wherein the polyol is selected from monosaccharides, oligosaccharides, alditols, 1,2-ethylene glycol, 1,2-propanediol, glycerol, 1,3-butanediol and polyethylene glycol having 2 to 20 ethylene glycol units.

19. The oxidation dyeing agent according to claim 4, wherein the mono- or oligosaccharide etherified with xylitol is selected from xylityl monoglucoside, xylityloligoglucoside having 2, 3, 4 or 5 consecutive glucose units, and mixtures thereof.

20. The oxidation dyeing agent according to claim 5, wherein the at least one intramolecular xylitol ether is 1,4-anhydroxylitol.

* * * * *